United States Patent
Zhang

(10) Patent No.: US 9,149,056 B2
(45) Date of Patent: Oct. 6, 2015

(54) COMPOSITIONS AND METHODS RELATING TO CAROTENOIDS

(75) Inventor: Jin Zhang, Clayton, OH (US)

(73) Assignee: The Iams Company, McLean, VA (US)

(*) Notice: Subject to any disclaimer, the term of this patent is extended or adjusted under 35 U.S.C. 154(b) by 0 days.

(21) Appl. No.: 13/347,849

(22) Filed: Jan. 11, 2012

(65) Prior Publication Data
US 2012/0184612 A1 Jul. 19, 2012

Related U.S. Application Data

(60) Provisional application No. 61/432,627, filed on Jan. 14, 2011.

(51) Int. Cl.
*A23K 1/16* (2006.01)
*A23K 1/18* (2006.01)

(52) U.S. Cl.
CPC ............. *A23K 1/1606* (2013.01); *A23K 1/1846* (2013.01)

(58) Field of Classification Search
USPC ............ 424/439, 442; 426/805; 119/174, 200
See application file for complete search history.

(56) References Cited

U.S. PATENT DOCUMENTS

| | | |
|---|---|---|
| 5,937,790 A | 8/1999 | Ito et al. |
| 6,133,323 A | 10/2000 | Hayek |
| 6,310,090 B1 | 10/2001 | Hayek |
| 2003/0082277 A1 | 5/2003 | Sokhey |
| 2003/0194478 A1 | 10/2003 | Davenport |
| 2003/0206972 A1 | 11/2003 | Babish et al. |
| 2004/0151761 A1 | 8/2004 | Chew |
| 2005/0118234 A1 | 6/2005 | Sunvold |
| 2005/0118299 A1 | 6/2005 | Vickers |
| 2005/0119222 A1 | 6/2005 | Norton |
| 2005/0123585 A1 | 6/2005 | Cox |
| 2005/0158367 A1 | 7/2005 | Hershberger |
| 2005/0208105 A1 | 9/2005 | Murray |
| 2005/0249837 A1 | 11/2005 | Massimino |
| 2005/0249841 A1 | 11/2005 | Hayek |
| 2005/0269218 A1 | 12/2005 | Sunvold |
| 2006/0127505 A1* | 6/2006 | Haines et al. ................ 424/729 |
| 2006/0228448 A1 | 10/2006 | Boileau |
| 2006/0260537 A1 | 11/2006 | Brent |
| 2006/0263416 A1 | 11/2006 | Brent |
| 2006/0263487 A1 | 11/2006 | Brent |
| 2007/0218164 A1 | 9/2007 | Stojanovic |
| 2007/0243297 A1 | 10/2007 | Keller |
| 2007/0243298 A1 | 10/2007 | Keller |
| 2007/0243299 A1 | 10/2007 | Keller |
| 2007/0251465 A1 | 11/2007 | Shafer |
| 2007/0286912 A1 | 12/2007 | Zhang |
| 2007/0286925 A1 | 12/2007 | Zhang |
| 2008/0124391 A1 | 5/2008 | Evans et al. |
| 2008/0175949 A1 | 7/2008 | Horgan |
| 2008/0175955 A1 | 7/2008 | Horgan |
| 2008/0175957 A1 | 7/2008 | Horgan |
| 2009/0181901 A1* | 7/2009 | Eidenberger ................... 514/18 |
| 2009/0220640 A1 | 9/2009 | Xu et al. |
| 2010/0003368 A1 | 1/2010 | Kerr |
| 2010/0003369 A1 | 1/2010 | Ter Haar |
| 2010/0233320 A1 | 9/2010 | Sunvold |
| 2010/0233756 A1 | 9/2010 | Sunvold |
| 2010/0303966 A1 | 12/2010 | Sunvold |
| 2010/0303968 A1 | 12/2010 | Sunvold |
| 2011/0027343 A1 | 2/2011 | Horgan |
| 2011/0027416 A1 | 2/2011 | Sunvold |
| 2011/0027417 A1 | 2/2011 | Corrigan |
| 2011/0027418 A1 | 2/2011 | Horgan |
| 2011/0027419 A1 | 2/2011 | Sunvold |
| 2011/0027420 A1 | 2/2011 | Mehansho |

FOREIGN PATENT DOCUMENTS

| | | |
|---|---|---|
| DE | 10 2007 001156 A1 | 7/2008 |
| JP | 54-070995 A | 6/1979 |
| WO | WO 2005/009422 A1 | 2/2005 |

OTHER PUBLICATIONS

R. Todd Lorenz, "A Technical Review of *Haematococcus* Algae", (Mar. 30, 1999).*
X002672250—"Feed for Culture of Red Sea-Bream—Contg. Colouring Agents to Give Improved Fish Colour", Database WPI Week 197929, Thomson Scientific, London, GB; AN 1979-53307B.
PCT International Search Report and Written Opinion for PCT/US2012/020852, dated Apr. 24, 2012—12 pages.
Mark L. Failla, et al., "In Vitro Models as Tools for Screening the Relative Bioavailabilities of Provitamin A Carotenoids in Foods"—HarvestPlus 3, 2005—pp. 1-32.
Chureeporn Chitchumroonchokchai et al., Assessment of Lutein Bioavailability from Meals and a Supplement Using Simulated Digestion and Caco-2 Human Intestinal Cells—The Journal of Nutrition, vol. 134, pp. 2280-2286.
Wan-Chin Lin et al., "Determination of Carotenoids in Spear Shrimp Shells (Parapenaeopsis hardwickii) by Liquid Chromatography"—Journal of Agricultural and Food Chemistry, vol. 32, 2005, pp. 5144-5149.
B. P Chew et al., "Uptake of B-Carotene by Blood Plasma and Lymphocytes in Cats"—FASEB Journal, 1997, Paragraph 2584.
B. S. Weng et al., "B-Carotene Uptake Plasma and Leukocytes in Dogs"—FASEB Journal, 1997, Paragraph 1046.
H. W. Kim et al., "Modulation of Cell-Mediated Immunity by Dietary Lutein in Dogs"—FASEB Journal, 1998, Paragraph 5598.
Hong Wook Kim et al., "Modulation of Humoral and Cell-Mediated Immune Responses by Dietary Lutein in Cats"—Veterinary Immunology and Immunopathology, vol. 73, 2000, pp. 331-341.
Honk Wook Kim et al., "Dietary Luetein Stimulates Immune Response in the Canine"—Veterinary immunology and Immunopathology, vol. 74, 2000, pp. 315-327.
B. P. Chew et al., "Dietary Astaxanthin Stimulates Cell-Mediated and Humoral Immune Response in Cats"—Experimental Biology 2004, Abstract—1 page.

(Continued)

*Primary Examiner* — Ernst V Arnold
*Assistant Examiner* — Kyung Sook Chang
(74) *Attorney, Agent, or Firm* — Tracey S. Truitt; Polsinelli PC

(57) ABSTRACT

A pet food composition having at least two carotenoids. The carotenoids can include a keto-carotenoid and at least one non-keto-carotenoid. The keto-carotenoid can include astaxanthin. The keto-carotenoid can include astaxanthin ester. The non-keto-carotenoid can include beta-carotene and/or lutein.

1 Claim, No Drawings

(56) References Cited

OTHER PUBLICATIONS

J. Park et al., "Dietary Beta-Carotene Enhances Cell-Mediated and Humoral Immune Response in Cats"—Experimental Biology 2004, Abstract—1 page.

B. P Chew et al., "Role of Dietary B-Carotene in Modulating Cell-Mediated and Humoral Immune Responses in Dogs"—FASEB Journal, 1997, Paragraph 5599.

B. P Chew et al., "B-Carotene Uptake by Corpus Luteum and Uterus and Changes in Ovarian Steroids and Uterine Proteins During the Estrous Cycle in Dogs"—FASEB Journal, 1997, Paragraph 5600.

N. Craft et al., "Carotenoids, Tocopherols and Vitamin A in Human Brain"—FASEB Journal, 1997, Paragraph 5601.

L. Kohlmeier et al., "Smoking and Carotenoid Isoforms in Serum"—FASEB Journal, 1997, Paragraph 5602.

M. G. Ferruzzi et al., "Carotenoid Determination in Biological Microsamples Using Liquid Chromatography with a Coulometric Electrochemical Array Detector"—FASEB Journal, 1997, Paragraph 5603.

A. During et al., "B-Carotene Conversion to Retinal is Associated with Copper and/or Iron Levels in Rat Small Intestine"—FASEB Journal, 1997, Paragraph 5604.

Chitchumroonchokchai, et al., "Assessment of Lutein Bioavailability from Meals and a Supplement Using Simulated Digestion and Caco-2 Human Intestinal Cells"—The Journal of Nutrition, vol. 134(9), pp. 2280-2286, Sep. 1, 2004.

\* cited by examiner

COMPOSITIONS AND METHODS RELATING TO CAROTENOIDS

CROSS REFERENCE TO RELATED APPLICATIONS

This application claims the benefit of U.S. Provisional Patent Application No. 61/432,627, filed Jan. 14, 2011, which is hereby incorporated by reference in its entirety.

FIELD

Embodiments of the invention relate to compositions and methods utilizing carotenoids. More particularly, but not exclusively, embodiments of the invention relate to pet food compositions and methods related to increasing the bioavailability of the carotenoids.

BACKGROUND

The bioavailability of carotenoids from diets can be affected by a complex number of factors such as physicochemical properties of the various carotenoids (free vs. esterified; hydrocarbon vs. oxygenated); their physical state (crystals vs. protein bound vs. solubilized in oil); dietary factors, e.g. amounts and types of fat and fiber; nutritional and physiologic status of the subject, and genotype. Additionally, carotenoid interactions at the intestinal level may reduce absorption of either of the carotenoids. Competition for absorption may occur at the level of micellar incorporation, intestinal uptake, lymphatic transport, or at more than one level. For example, beta-carotene was reported to decrease lutein absorption, whereas lutein decreased beta-carotene absorption in some human subjects but increased it in others (See Kostic D, White W S, Olson J A. Intestinal absorption, serum clearance, and interactions between lutein and β-carotene when administered to human adults in separated or combined oral doses. Am J Clin Nutr. 1995; 62:604-610). In another study, lutein impaired beta-carotene absorption by human subjects but did not affect the secretion of retinyl esters in chylomicrons (See van den Berg H, van Vliet T. Effect of simultaneous, single oral doses of 13-carotene with lutein or lycopene on the β-carotene and retinyl ester responses in the triglyceride-rich fraction of men. Am J Clin Nutr 1998; 68:82-89). In contrast, beta-carotene absorption was not affected by lycopene in these subjects. Additional reports of interactions between pure carotenoids that affect their postprandial appearance in plasma of humans and animals have been reviewed by van den Berg (See van den Berg H. Carotenoid interactions. Nutr Rev. 1999; 57:1-10.). Tyssandier et al. reported that the absorption of beta-carotene, lutein, and lycopene from a single vegetable was greater when the food was administered alone than when it was co-administered with either a second carotenoid-rich vegetable or the purified carotenoid that was enriched in the second vegetable (See Tyssandier V, Reboul E, Dumas J, Bouteloup-Demange C, Armand M, Marcand J, Sallas M, Borel P. Processing of vegetable-borne carotenoids in human stomach and duodenum. Am J Physiol (Gastrointest Liver Physiol). 2003; 284: G913-G922).

Early studies have reported that both the canine and domestic feline are unable to absorb beta-carotene from the diet (Goodwin T. Mammalian carotenoids. In: Goodwin T W, ed. The comparative biochemistry of the carotenoids. London: Chapman and Hall Ltd., 1952; 229-269). Recently, several systematic studies indicated that dogs and cats can absorb beta-carotene and lutein (Weng B C, Chew B P, Park J S, Wong T S, Combs R L, Hayek M G, Reinhart G A. β-Carotene uptake by blood plasma and leukocytes in dogs. FASEB J 1997; 11:A180 Kim H W, Chew B P, Wong T S, Park J S, Weng B B, Byrne K M, Hayek M G, Reinhart G A. Dietary lutein stimulates immune response in the canine. Vet Immunol Immunopathol. 2000 May 23; 74(3-4):315-27. Chew B P, Weng B C, Park J S, Wong T S, Combs R L, Hayek M G, Reinhart G A. Uptake of β-carotene by blood plasma and lymphocytes in cats. FASEB J 1997; 11:A447. Kim, H. W., Chew, B. P., Wong, T. S., Park, J. S., Weng, B. C., Byrne, K. M., Hayek, M. G. & Reinhart, G. A. Modulation of humoral and cell-mediated immune responses by dietary lutein in cats. Vet. Immunol. Immunopath. 2000, 73:331-341). However, it is unknown how carotenoids interact with each other in dogs and cats. A beneficial effect between the carotenoids is desired if used in companion animals because it is believed that each individual carotenoid has a potential role in contributing to the health of dogs and cats. Thus, a product is desired that would combine carotenoids in a way to positively affect the absorption of those carotenoids. Such a product could then exhibit more beneficial effects on the animal.

SUMMARY

In one embodiment, a pet food composition comprising at least three carotenoids is disclosed. The carotenoids can comprise a keto-carotenoid, a first non-keto-carotenoid, and a second non-keto-carotenoid. The keto-carotenoid can comprise astaxanthin. The keto-carotenoid can comprise astaxanthin ester. The first non-keto-carotenoid can comprise beta-carotene. The second non-keto-carotenoid can comprise lutein. The keto-carotenoid can be present at from about 0.1% to about 25% by weight of the carotenoids, the first non-keto-carotenoid can be present at up to about 99.9% by weight of the carotenoids, and the second non-keto-carotenoid can be present at up to about 99.9% by weight of the carotenoids. The pet food composition can be selected from the group consisting of a nutritionally balanced kibble, a supplement, a treat, a biscuit, a wet composition, and combinations and mixtures thereof.

In another embodiment, a pet food composition is disclosed that can comprise at least two carotenoids. The two carotenoids can comprise either astaxanthin or astaxanthin ester and a non-keto-carotenoid. The non-keto-carotenoid can comprise beta-carotene or lutein. The ratio of the non-keto-carotenoid to astaxanthin can be from about 25:75 to about 90:10. The pet food composition can be selected from the group consisting of a nutritionally balanced kibble, a supplement, a treat, a biscuit, a wet composition, and combinations and mixtures thereof.

In another embodiment, a method to increase the bioavailability of a non-keto-carotenoid in a companion animal is disclosed. The method can comprise administering to the companion animal the pet food composition, wherein the administering occurs such that from about 2 mg to about 100 mg of carotenoids daily are delivered to the companion animal.

DETAILED DESCRIPTION

Definitions

As used herein, the articles including "the", "a", and "an", when used in a claim or in the specification, are understood to mean one or more of what is claimed or described.

As used herein, the terms "include", "includes", and "including" are meant to be non-limiting.

As used herein, the term "plurality" means more than one.

As used herein, the terms "animal" or "pet" mean a domestic animal including, but not limited to domestic dogs (canines), cats (feline), horses, cows, ferrets, rabbits, pigs, rats, mice, gerbils, hamsters, horses, and the like. Domestic dogs and domestic cats are particular examples of pets and are referred to herein as "companion animals." It should be understood that throughout this disclosure when using the term animal, pet, or companion animal, the animal, pet, or companion animal is in a non-diseased state, unless otherwise stated.

As used herein, the terms "animal feed", "animal feed compositions", "animal feed kibble", "pet food", or "pet food composition" all mean a composition intended for ingestion by a pet. Pet foods can include, without limitation, nutritionally balanced compositions suitable for daily feed, as well as wet food, supplements, and/or treats, which may or may not be nutritionally balanced.

As used herein, the term "nutritionally balanced" means that a composition, such as pet food, has known required nutrients to sustain life in proper amounts and proportions based on recommendations of recognized authorities, including governmental agencies, such as, but not limited to, Unites States Food and Drug Administration's Center for Veterinarian Medicine, the American Feed Control Officials Incorporated, in the field of pet nutrition, except for the additional need for water.

As used herein, the term "orally administering" with respect to the companion animal means that the animal ingests or a human is directed to feed, or does feed, the animal one or more compositions herein.

As used herein, the term "absorption" means, such as in the case of a dietary component (such as carotenoids as disclosed herein) from food, that the dietary component is digested in the gastric intestinal space and passes into the blood vessels in the wall of the intestine through the process of diffusion, in a companion animal, for instance.

As used herein, the term "bioavailability" means the absorption of a dietary component from food for utilization or storage in the body. Dietary components ingested but not released during the digestive process for absorption are of limited to no nutritional value. The delivery of ingested dietary components and their bioactive metabolites to target tissues is dependent on absorption from the small intestine. Therefore, bioavailability can also be considered the relative absorption of a dietary component from the food.

As used herein, the terms absorption and bioavailability can be interchangeable.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All lists of items, such as, for example, lists of ingredients, are intended to and should be interpreted as Markush groups. Thus, all lists can be read and interpreted as items "selected from the group consisting of" . . . list of items . . . "and combinations and mixtures thereof."

Referenced herein are trade names for components including various ingredients utilized in embodiments of the invention. The inventors herein do not intend to be limited by materials under a certain trade name. Equivalent materials (e.g., those obtained from a different source under a different name or reference number) to those referenced by trade name may be substituted and utilized in the descriptions herein.

The processes, methods, compositions, and apparatuses herein may comprise, consist essentially of, or consist of any of the features or embodiments as described herein.

In the description of the various embodiments of the disclosure, various embodiments or individual features are disclosed. As will be apparent to the ordinarily skilled practitioner, all combinations of such embodiments and features are possible and can result in preferred executions of the disclosure. While various embodiments and individual features of the invention have been illustrated and described, various other changes and modifications can be made without departing from the spirit and scope of the invention. As will also be apparent, all combinations of the embodiments and features taught in the foregoing disclosure are possible and can result in preferred executions of the invention.

Embodiments of the Invention

In some embodiments, the invention relates to compositions and methods that increase the bioavailability of dietary carotenoids.

As described herein, absorption of a dietary component, such as beta-carotene, lutein, and/or astaxanthin, from food means that the dietary component is digested in the gastric intestinal space and passes into the blood vessels in the wall of the intestine through the process of diffusion. Absorption is used interchangeably herein with bioavailability, which generally means the absorption of a dietary component from food for utilization or storage in the body. Dietary components ingested but not released during the digestive process for absorption are of limited to no nutritional value. The delivery of ingested dietary components and their bioactive metabolites to target tissues is dependent on absorption from the small intestine. Therefore, bioavailability can also be considered the relative absorption of a dietary component from the food.

Carotenoids are a class of hydrocarbons consisting of eight isoprenoid units joined in a head-to-tail pattern, except at the center, to give symmetry to the molecule so that the two central methyl groups are in a 1,6-positional relationship, and the remaining non-terminal methyl groups are in a 1,5-positional relationship. Based on this structure, a semi-systematic numbering system is used, and carotenoids are named as a derivative of their parent compound. Greek letters are used to describe the end groups of the structure in the IUPAC system. The position of hydrogenation and group substitution is indicated by prefixes and suffixes. The majority of carotenoids are derived from a 40-carbon polyene chain, which is typically considered as the backbone of the molecule. This chain may be terminated by cyclic end-groups (rings) and may be complemented with oxygen containing functional groups. All carotenoids can be considered as Lycopene ($C_{40}H_{56}$) derivatives by reactions involving: (1) hydrogenation, (2) dehydrogenation, (3) cyclization, (4) oxygen insertion, (5) double bond migration, (6) methyl migration, (7) chain elongation, and (8) chain shortening. Based on their chemical structure, carotenoids are classified into two groups: hydrocarbons commonly known as carotenes that are constituted by carbon and hydrogen; and oxycarotenoids or xanthophylls that are have carbon, hydrogen, and additionally oxygen. The examples of carotenes are α-Carotene, β-Carotene, γ-Carotene, δ-Carotene, ε-Carotene, ζ-Carotene, Lycopene, Neurosporene, Phytoene, and Phytofluene. The oxygenated carotenoids or xanthophylls can be further classified as those containing a hydroxyl group only (termed here as hydroxyl xanthophylls), such as Lutein, Zeaxanthin, Cryptoxanthin, Antheraxanthin, Neoxanthin, and Violaxanthin; and those having a keto group with or without the hydroxyl group (termed here as keto xanthophylls), such as Astaxanthin, Canthaxanthin, and Fucoxanthin. The carotenoids without a keto group are called non-keto carotenoids herein (such as beta-carotene and lutein), while the carotenoids having a keto group are called keto-carotenoids herein (such as astaxanthin).

Astaxanthin is a keto-carotenoid and classified as a keto-xanthophyll. Like many carotenoids, it is a colorful, lipid-soluble pigment. Astaxanthin is found in microalgae, yeast, salmon, trout, krill, shrimp, crayfish, crustaceans, and the feathers of some birds. The commercial production of astaxanthin comes from both natural and synthetic sources. Synthetic astaxanthin is produced as free (unesterified) astaxanthin in a mixture of stereoisomers: the stereoisomers (3R, 3'R), (3R,3'S), and (3S,3'S) occur in a ratio of 1:2:1. Natural astaxanthin, on the other hand, is usually esterified and predominantly of (3S,3'S) configuration or, less frequently, mainly (3R,3'R). Currently, the primary natural source for astaxanthin is the microalgae *Haematococcus pluvialis*. In *Haematococcus pluvialis*, astaxanthin occurs as the 3S,3'S stereoisomer and primarily as monoesters (>90%), with diesters comprising ~8% and the free molecule ~1% (Renstrøm et al. 1981). Another natural source is from Phaffia yeast. Phaffia yeast xanthophyllomyces dendrorhous exhibits 100% or nearly 100% free astaxanthin in 3R,3'R, and non-esterified form. One suitable source of free astaxanthin is described at http://www.naturxan.com/products/aquasta/natural-vs-synthetic.html. As used herein, when the term astaxanthin is used as part of a composition, it can also mean astaxanthin-ester.

Beta-carotene, a naturally-occurring hydrocarbon carotenoid, can be found in orange root vegetables such as carrots and yams and in green leafy vegetables such as spinach, kale, and sweet potato leaves. Among other sources, it is also commercially available in synthetic or natural forms from palm oil, algae, or fungi. For most mammals, beta-carotene is a precursor to vitamin A, meaning that mammals can convert beta-carotene into vitamin A. Cats are a notable exception because they have a limited ability to do so. Beta-carotene is an antioxidant in addition to its pro-vitamin A activity. It can be used for humans as a food supplement to prevent cancer and heart disease and can boost immunity and support vision. It is also used in pet food as an antioxidant for providing immune benefits, among other benefits.

Lutein, a naturally-occurring oxycarotenoid that belongs to the class of xanthaphyll, can be found in green leafy vegetables such as spinach and kale. Among other sources, it is also commercially available synthetically or naturally from marigold extract, corn gluten meal, and corn kernel oil. Lutein is known for its benefit to eye health. It was found to be concentrated in the macula and helps protect the eye from oxidative stress and high-energy light. Lutein also provides benefits to cardiovascular health and skin health. Lutein has been used in pharmaceutical, nutraceutical, foods, pet foods, animal feeds, and fish feeds. It is also used in pet food as an antioxidant for providing immune benefits, among other benefits.

As used herein, when amounts or proportions of beta-carotene, lutein, and astaxanthin are described, the amount or proportion includes the total amounts of these ingredients, including all isomers and forms of these ingredients. For example, the cis- and trans-forms of beta-carotene are included in the amounts of beta-carotene.

Additionally, carotenoids are a subset of antioxidants, which are naturally-occurring plant pigments that commonly include beta-carotene, lutein, and astaxanthin, among others. In humans, carotenoids from fruit and vegetable consumption were associated with reduced risk of coronary heart disease and some types of cancer (See Van Poppel G. Epidemiological evidence for beta-carotene in prevention of cancer and cardiovascular disease. Eur. J. Clin. Nutr. 1996; 50:S57-S61). Carotenoids also have been found to be beneficial to companion animals, such as cats and dogs.

In dogs, it has been found that dietary beta-carotene and lutein increase cell-mediated and humoral immune responses in beagles (See Chew B P, Park J S, Wong T S, Weng B C, Kim H W, Byrne K M, Hayek M G, Reinhart G A. Role of dietary beta-carotene in modulating cell-mediated and humoral immune responses in dogs. FASEB J 12:A967, 1998 and Kim H W, Chew B P, Wong T S, Park J S, Weng B C, Byrne K M, Hayek M G. Modulation of cell-mediated immunity by dietary lutein in dogs. FASEB J 1998; 12:A966). It has been found that astaxanthin shows immuno-modulating benefits in dogs, including increased cell-mediated and humoral immune responses; reduced DNA damage, and inflammation in dogs (See United States Patent Publication No. 2004/0151761).

In cats, it has been found that dietary lutein increases DTH response to both specific and nonspecific antigens (Park, J. S., Chew, B. P., Hayek, M. G., Massimino, S. & Reinhart, G. A. (2004). Dietary beta-carotene enhances cell-mediated and humoral immune response in cats. FASEB J. 18: A53). Additionally, it has been found that cats fed astaxanthin show enhanced cell-mediated and humoral immune responses (See United States Patent Publication No. 20040151761 and Chew B P, Park J S, Hayek M G, Reinhart G A. Dietary astaxanthin stimulates cell-mediated and humoral immune response in cats. FASEB J 2003).

Embodiments of the present invention relate to compositions comprising particular amounts of carotenoids. Specific embodiments relate to the carotenoids astaxanthin, beta-carotene, and lutein. As described herein, these specific carotenoids provide health benefits to companion animals. Additionally, it has been determined that particular combinations of the carotenoids can increase the absorption, or bioavailability, of the carotenoids.

The compositions herein can be adapted for use by a companion animal, such as dogs and cats, for example. In this respect, as will be well-understood by the ordinarily skilled artisan, the primary use of the compositions described herein is for companion animal use and the compositions are therefore formulated as such. The compositions used herein can be pet food compositions. These will advantageously include foods intended to supply necessary dietary requirements, as well as treats (e.g., biscuits) or other food supplements. The composition herein may be a pet food composition such as a dry composition (for example, kibble), semi-moist composition, wet composition, or any mixture thereof. Alternatively or additionally, the composition can be a supplement, such as a gravy, drinking water, yogurt, powder, suspension, chew, treat (e.g., biscuits), powder to be sprinkled, or any other delivery form. As an example, in one embodiment the composition can be nutritionally balanced and can be a nutritionally balanced kibble.

The compositions described herein may be used as a supplement to ordinary dietetic requirements or may serve as the primary food for the companion animal (and, as such, the supplements or foods may be nutritionally balanced). Administration may be on as as-needed or as-desired basis, for example, once-monthly, once-weekly, or daily (including multiple times daily). When utilized as a supplement to ordinary dietetic requirements, the composition may be administered directly to the mammal or otherwise contacted with or admixed with daily feed or food or water. When utilized as a daily feed or food, administration will be well-known to those of ordinary skill.

The compositions used herein may comprise one or more further components. In one embodiment, the compositions may comprise, on a dry matter basis, from about 10% to about 90% crude protein, alternatively from about 20% to about 50% crude protein, alternatively from about 20% to about 40% crude protein, by weight of the composition, or alternatively from about 20% to about 35% crude protein, by weight of the composition. The crude protein material may comprise vegetable-based proteins such as soybean, cereals (corn, wheat, etc), cottonseed, and peanut, or animal-based proteins such as casein, albumin, and meat protein. Non-limiting examples of meat protein useful herein include a protein source selected from the group consisting of beef, pork, lamb, poultry, fish, and mixtures thereof.

Furthermore, the compositions may comprise, on a dry matter basis, from about 5% to about 40% fat, alternatively from about 10% to about 35% fat, by weight of the composition.

Embodiments related to compositions of the invention may further comprise a source of carbohydrate. In one embodiment, the compositions may comprise from about 35%, by weight of the composition, up to about 50%, by weight of the composition, carbohydrate source. In other embodiments, the composition can comprise from about 35% to about 45%, by weight of the composition, or from about 40% to 50%, by weight of the composition, carbohydrate source. Grains or cereals such as rice, corn, milo, sorghum, barley, wheat, and the like are illustrative sources of carbohydrate.

The compositions may also contain other materials such as, but not limited to, dried whey and other dairy by-products, beet pulp, cellulose, fiber, fish oil, flax, vitamins, minerals, flavors, antioxidants, and taurine.

The compositions may also contain other optional ingredients. Optional ingredients can include Probiotic components (Bifidobacteria and/or *Lactobacillus*) and Prebiotic (fructooligosaccharides) components. Examples and amounts of Probiotic components and Prebiotic components that can be included are disclosed in United States Publication No. 2005/0158294, for example. Other optional ingredients that can be included are omega 6 and omega 3 fatty acids, carnitine, hexametaphosphate, glucosamine, and chondroitin sulfate. The compositions may also comprise at least one fiber source for improved gastrointestinal health. Such fiber sources may comprise, for example, at least one moderately fermentable fiber. Moderately fermentable fiber has previously been described to provide a benefit to the immune system of a companion animal. Moderately fermentable fiber or other compositions known to those of skill in the art which provide a prebiotic composition to enhance the growth of Probiotic microorganisms within the intestine may also be incorporated into the composition to aid in the enhancement of the benefit provided by the present invention to the immune system of an animal. Additionally, Probiotic microorganisms, such as *Lactobacillus* or *Bifidobacterium* species, for example, may be added to the composition.

Other optional ingredients can include tea, such as green tea, black tea, oolong, or white tea; alphalipoic acid and its salts; herbs and spices and essential oils derived from herbs and spices; vitamin E at from about 100 mg to about 2000 mg per kg composition; vitamin C (ascorbic acid); selenium; rosemary extract; isoflavones; chromium; fruits; and vegetables.

The methods of the present invention comprise orally administering (i.e., through ingestion) a composition of the present invention to a companion animal and most preferably a domestic dog or cat. If a human is directed to feed the composition, such direction may be that which instructs and/or informs the human that use of the composition may and/or will provide a benefit, for example, attenuation of inflammation or enhanced immune response. For example, such direction may be oral direction (e.g., through oral instruction from, for example, a physician, veterinarian, or other health professional; or radio or television media, i.e., advertisement; or written direction from, for example, a physician, veterinarian, or other health professional, e.g., scripts, or sales professional or organization, e.g., through, for example, marketing brochures, pamphlets, or other instructive paraphernalia; other written media, e.g., internet, electronic mail, or other computer-related media; and/or packaging associated with the composition, e.g., a label present on a container holding the composition. As used herein, "written" means through words, pictures, symbols, and/or other visible descriptors. Such information need not utilize the actual words used herein, for example, "attenuate", "inflammation", "enhance", "immune", "response", or the like, but rather use of words, pictures, symbols, and the like conveying the same or similar meaning are contemplated within the scope of this invention.

The amount of composition utilized may be dependent on a variety of factors, including the condition and/or age of the companion animal, the quality of the pet food composition or supplement (where applicable), and size or breed of the companion animal (where applicable).

Thus, disclosed herein is a pet food composition comprising at least three carotenoids, the three carotenoids comprising a keto-carotenoid and a first non-keto-carotenoid and a second non-keto-carotenoid. The keto-carotenoid can comprise any of the keto-carotenoids disclosed herein, including astaxanthin and astaxanthin ester. The first and second non-keto-carotenoids can include any of the non-keto-carotenoids disclosed herein, including beta-carotene and lutein.

In one embodiment, the pet food composition can include two carotenoids, the two carotenoids comprising astaxanthin or astaxanthin ester with one non-keto-carotenoid.

As described, the embodiments of the present invention comprise compositions that include beta-carotene, lutein, and astaxanthin, in varying amounts, combinations, and/or ratios. Thus, these components can make up the total amount of carotenoids by weight of the overall composition. In one embodiment, the total amount of carotenoids, by weight of the composition is about 0.0025% for a nutritionally balanced pet food composition. In another embodiment, the total carotenoids, by weight of the composition, is from about 0.0005% to about 0.025% for a nutritionally balanced pet food composition. In another embodiment, the total carotenoids, by weight of the composition, is from about 0.0001% to about 0.01% for a nutritionally balanced pet food composition. In another embodiment, the total carotenoids, by weight of the composition, is from about 0.001% to about 0.01% for a nutritionally balanced pet food composition. In another embodiment, the total carotenoids, by weight of the composition, is from about 0.001% to about 0.005% for a nutritionally balanced pet food composition. In another embodiment, the total carotenoids, by weight of the composition, is from about 0.002% to about 0.003% for a nutritionally balanced pet food composition.

In another embodiment, the total carotenoids, by weight of the composition, can be about 0.0525% for a supplement, such as a biscuit. In another embodiment, the total carotenoids, by weight of the composition, is from about 0.01% to about 0.1% for a supplement, such as a biscuit. In another embodiment, the total carotenoids, by weight of the composition, is from about 0.02% to about 0.08% for a supplement, such as a biscuit. In another embodiment, the total carotenoids, by weight of the composition, is from about 0.04% to about 0.06% for a supplement, such as a biscuit.

In one embodiment, the beta-carotene, lutein, and astaxanthin can be combined in varying amounts relative to the total amount of carotenoids of the three. In one embodiment, the beta-carotene can comprise from 0% to about 99.9% by weight of the total carotenoids. In one embodiment, the lutein can comprise from 0% to about 99.9% by weight of the total carotenoids. In one embodiment, the astaxanthin can comprise from about 0.1% to about 25% by weight of the total carotenoids. In one embodiment, only one of beta-carotene and lutein is present in the composition along with astaxanthin. In one embodiment, all three of the carotenoids are present in the composition. In one embodiment, beta-carotene can be present at from about 30% to about 80%, or from about 40% to about 60%, or at about 50%, or at about 55%, by total weight of carotenoids. In one embodiment, lutein can be present at from about 10% to about 40%, or from about 20% to about 40%, or from about 25% to about 35%, or at about 25%, or at about 30%, by total weight of the carotenoids. In one embodiment, the astaxanthin can be present at from about 6% to about 25%, or from about 6% to about 25%, or from about 10% to about 25%, or at about 15%, or at about 20%, or at about 25%, by total weight of the carotenoids.

In one embodiment in which only one of beta-carotene and lutein can be present along with astaxanthin, the ratio of beta-carotene or lutein to astaxanthin can be from about 25:75 to about 90:10, or from about 40:60 to about 70:30, or from about 75:25 to about 90:10, or from about 80:20 to about 90:10, or about 50:50.

In one embodiment in which all three carotenoids beta-carotene, lutein, and astaxanthin can be present, the ratio of beta-carotene to lutein can be from about 1:10 to about 10:1, or from about 1:9 to about 9:1, or from about 1:8 to about 8:1, or from about 1:7 to about 7:1, or from about 1:6 to about 6:1, or from about 1:5 to about 5:1, or from about 1:4 to about 4:1, or from about 1:3 to about 3:1, or from about 1:2 to about 2:1, or about 2:1, or about 1:1, regardless of the amount of astaxanthin.

In one embodiment in which all three carotenoids beta-carotene, lutein, and astaxanthin are present, the ratio of beta-carotene to lutein to astaxanthin can be from about 1:1:0.6 to about 10:1:3.5, or from about 1:1:0.6 to about 1:10:3.5. In one embodiment in which all three carotenoids beta-carotene, lutein, and astaxanthin are present, the ratio of beta-carotene to lutein to astaxanthin can be from about 1:1:0.002 to about 10:1:0.01, or from about 1:1:0.002 to about 1:10: 0.01, or about 4:1:1.5, or about 2:1:1, or about 2:1:0.5.

In one embodiment, a method to increase the bioavailability of the carotenoids disclosed herein in a companion animal comprising administering to the companion animal the compositions disclosed herein. As described, a combination of the carotenoids can result in an increase in the bioavailability of the carotenoids when administered and consumed by companion animals.

In one embodiment, the total amount of carotenoids administered to the companion animal per day can be from about 2 mg to about 100 mg, or from about 2 mg to about 50 mg, or from about 2 mg to about 20 mg. In one embodiment, the total amount of carotenoids administered to the companion animal per day is about 20 mg. Of course, as is known in the art, these amounts can vary depending on the type and size of companion animal that the composition is being administered to. For example, with dogs, a giant breed may be administered about 20 mg of total carotenoids per day, large breeds may be administered about 12-13 mg of total carotenoids per day, medium breeds may be administered about 4-5 mg of total carotenoids per day, and small breeds may be administered about 2 mg of total carotenoids per day. Small breed may refer to a dog having a body weight less than 20 pounds, medium breed may refer to a dog having a body weight between 20 to 50 pounds, large breed may refer to body weight between 50 to 90 pounds, giant breed refers body weight more than 90 pounds. Within the total amount of carotenoids, the individual carotenoids themselves can be administered in varying amounts. In one embodiment, beta-carotene can be administered at from about 1 mg to about 50 mg per day, or from about 1 mg to about 20 mg per day, or from about 1 mg to about 15 mg per day, or from about 2 mg to about 10 mg per day, or about 1 mg per day, or about 2 mg per day, or about 5 mg per day. In one embodiment, lutein can be administered at from about 1 mg to about 50 mg per day, or from about 1 mg to about 20 mg per day, or from about 1 mg to about 15 g per day, or from about 2 mg to about 10 mg per day, or about 1 mg per day or about 2 mg per day, or about 5 mg per day. In one embodiment, astaxanthin can be administered at from about 0.001 mg to about to about 25 mg per day, or from about 0.01 mg to about 25 mg per day, or from about 0.1 mg to about 20 mg per day, or from about 0.1 mg to about 10 mg per day, or from about 0.5 mg to about 5 mg per day, or from about 0.5 to about 2.5 mg per day, or from about 1 mg to about 2.5 mg per day, or from about 1 mg to about 2 mg per day, or about 1 mg per day, or about 2 mg per day, or about 5 mg per day. Of course, these individual carotenoids can also vary based on the type and breed of companion animal as well.

EXAMPLES

Example 1

Carotenoid Supplementation—In Vivo

Eighteen (18) spayed/neutered Rottweilers (5-6 years old) were randomized into three groups. One group served as the control group and received control biscuits without beta-carotene, lutein, or astaxanthin, while the other two groups received biscuits containing antioxidant cocktails as follows: one group received beta-carotene and lutein containing biscuits (BL), and the other group received beta-carotene, lutein, and astaxanthin containing biscuits (BLA). All dogs were on a diet of Jams® Large Breed Diet (Vitamin E GA level=140 IU). The biscuits were used to deliver daily dose of carotenoids. Each dog was given four biscuits per day to feed desired levels of carotenoids. The biscuits were about 10-12 grams in size.

The control biscuits were Eukanuba® Healthy Extra Adult Maintenance biscuits.

The beta-carotene and lutein containing biscuits were Eukanuba® Healthy Extra Adult Maintenance biscuits. The biscuits were fed to the dogs such that the dogs consumed 21.36 mg per day of beta-carotene and lutein combined and in ratio of 63:37 beta-carotenes to lutein.

The beta-carotene, lutein, and astaxanthin containing biscuits were Eukanuba® Healthy Extra Adult Maintenance biscuits. The biscuits were fed to the dogs such that the dogs consumed 21.55 mg per day of beta-carotene, lutein, and astaxanthin and in a ratio of 61:16:23 beta-carotene to lutein to astaxanthin.

Table 1 shows a carotenoids summary for the Rottweilers consuming the BL biscuits (treat 1) and the BLA biscuits (treat 2). The control biscuit was used to measure and compare physiological measurements of the dogs. As the table shows, the dogs consumed approximately the same amount of carotenoids per day (21.36 versus 21.55), but treat 1 only provided beta-carotene and lutein while treat 2 provided beta-carotene, lutein, and astaxanthin. Accordingly, the ratio of the individual carotenoids was different as well, as is shown by Table 1. It should be noted that the astaxanthin in this example was a mixture of astaxanthin and astaxanthin esters.

TABLE 1

Carotenoid Absorption

|  | Total Carotenoids fed mg/day/ dog | Carotenoid Ratio | Serum Conc in nM/L per mg of Carotenoid fed | | % Increased Absorption | |
|---|---|---|---|---|---|---|
|  |  |  | B | L | B | L |
| Treat 1 | 21.36 | B:L::63:37 | 0.73 | 2.25 | 0 | 0 |
| Treat 2 | 21.55 | B:L:A::61:16:23 | 1.48 | 5.46 | 102.02 | 142.27 |

As shown in Table 1, carotenoids were able to be absorbed by the Rottweilers consuming the treat 1 and treat 2 biscuits and reached the systemic circulation. Serum carotenoids were measured by HPLC in Rottweilers after six weeks of carotenoid supplement in the form of the biscuits. The serum concentration is shown in Table 1.

Dogs consuming treat 1 received total carotenoids of 21.36 mg/day with approximately 13.5 mg/day of beta-carotene (B) and approximately 7.8 mg/day of lutein (L). These amounts resulted in a beta-carotene to lutein ratio of about 63:37 as fed. Dogs consuming treat 2 received total carotenoids of 21.55 mg/day with approximately 13.2 mg/day of beta-carotene (B), approximately 3.4 mg/day of lutein (L), and approximately 4.9 mg/day of astaxanthin (A). These amounts resulted in a beta-carotene to lutein to astaxanthin ratio of about 61:16:23, with astaxanthin comprising about 23% of the total carotenoids as fed.

Accordingly, keeping the total amount of carotenoids approximately the same for treat 1 and treat 2, and with the addition of astaxanthin into treat 2, the beta-carotene absorption increased by about 102% (1.48 versus 0.73), and the lutein absorption increased by about 142% (2.25 versus 5.46) when compared with treat 1 containing no astaxanthin, as measured by the serum concentration.

Additionally, the change of sensitivity of peripheral blood lymphocytes (PBL) to ex vivo $H_2O_2$ challenge, as a marker of susceptibility to DNA damage, was conducted for the dogs in this example. The tested PBLs of the dogs consuming the beta-carotene, lutein, and astaxanthin containing biscuits experienced reduced DNA damage by 5.2% compared to baseline, which is before the dogs started consuming the biscuits. However, the tested PBLs of the dogs on a beta-carotene and lutein containing biscuit experienced reduced DNA damage by only 2.4%. These are in comparison to a 10.1% increase in DNA damage to tested PBLs of dogs consuming the control biscuits, which contained no beta-carotene, lutein, or astaxanthin. Thus, as is evidenced by this example, while both beta-carotene and lutein and beta-carotene, lutein, and astaxanthin containing biscuits helped to protect PBLs from DNA damage, the beta-carotene, lutein, and astaxanthin containing biscuit provided a greater protection. This example is reflective of reduced susceptibility of DNA damage in the dogs consuming the carotenoid containing biscuits and thus a reduction of oxidative stress.

In vitro, the cellular uptake of carotenoids coupling in vitro digestion with Caco-2 cell model was used to examine cellular acquisition of micellarized carotenoids from digested food and therefore predict absorption of carotenoids from food/diet. These are shown in Examples 2, 3, and 4.

Example 2

Carotenoids—In Vitro Absorption

An in vitro digestion coupled with intestinal culture model was developed to mimic the in vivo absorption of carotenoids. It is important to note that absorption as determined by in vitro digestion is highly correlated with data derived by sampling small intestinal luminal contents from human subjects fed carotenoid rich vegetables and bioavailability data from published human studies.

The interactions among beta-carotene (B), lutein (L), and astaxanthin (A) or astaxanthin ester (AE) were examined using the coupled simulated digestion/Caco-2 cell model. Cellular carotenoids after four hour incubation with micelles generated during simulated digestion of carotenoid-rich oil are presented in Table 2 below.

In BLA (A is 25% of total carotenoids), B cellular uptake is 8.59% and increased by 50.6% compared to B uptake in B alone; L uptake is 6.37% and increased by 5.88% compared to L uptake in L alone. In BLAE (AE is 25% of total carotenoids), B cellular uptake is 12.09% and increased by 112.05% compared to B cellular uptake in B alone; L cellular uptake is 12.18% and increased by 102.35% compared L cellular uptake in L alone.

% Carotenoid Cellular Uptake=(carotenoid in cells/carotenoid added in the test food)*100%.

TABLE 2

In-Vitro Carotenoid Cellular Uptake

|  | Added Amt | Carotenoid | % Carotenoid Cellular Uptake | | % Increase in Carotenoid Cellular Uptake | |
|---|---|---|---|---|---|---|
|  | nmol/50 ml | Ratio | B | L | B | L |
| Beta-carotene | 205.1 | 100 | 5.70 | NA | 0.00 | NA |
| Lutein | 193.5 | 100 | NA | 6.02 | NA | 0.00 |
| B:L:A | 201.2 | 51:24:25 | 8.59 | 6.37 | 50.60 | 5.88 |
| B:L:AE | 201.2 | 51:24:25 | 12.09 | 12.18 | 112.05 | 102.35 |
| B:A | 203.2 | 51:50 | 5.49 | NA | −3.77 | NA |
| L:A | 197.4 | 48:50 | NA | 5.76 | NA | −4.33 |
| L:AE | 197.4 | 48:50 | NA | 9.05 | NA | 50.35 |

Simulated digestion: Non-fat yogurt (2.7 g) was homogenized in 10 mL 120 mM salt solution. The mixture was transferred to 50 mL glass test tube. Carotenoid rich oil was carefully added for each reaction (6 replicates per test oil), and total volume of oil was adjusted to 300 μL using soybean oil. The procedure for the simulated digestion followed the standard protocol (See Failla M L., Chitchumroonchokchai C. (2005) In vitro models as tools for screening the relative bioavailabilities of provitamin A carotenoids in foods. HarvestPlus Technical Monograph Series 3. 32 p. www.harvestplus.org/pdfs/tech03.pdf), except that reactions contained pancreatic enzymes and bile extract. Simulated digestion without bile extract also was conducted to demonstrate that transfer of carotenoids from the oil to the aqueous fraction was bile dependent. After completing gastric and small intestinal digestion, an aliquot (9 ml.) of digesta was centrifuged at 12,000×g, 4° C. for 45 min. to isolate aqueous fraction containing micellar carotenoids from residual undigested materials. The aqueous fraction was passed through syringe filter (0.22 μm) to determine carotenoids that partitioned into either aqueous or micellar phase. Aliquots of digesta and aqueous fraction were stored at −20° C. for a maximum of one week before extraction. Beta-carotene and lutein was quantified according to Chitchumrronchokchai et al. (See Chitchumroonchokchai C., Schwartz S J., Failla M L. Assessment of lutein bioavailability from meals and supplement using simulated digestion and Caco-2 human intestinal cells. J Nutr. 2004; 134:2280-2286), and astaxanthin was measured as described in Lin W C et al. (Lin W C, Chien J T, Chen B H. Determination of carotenoids in spear shrimp shells (*Parapenaeopsis hardwickii*) by liquid chromatography. J Agric Food Chem. 2005 Jun. 29; 53(13):5144-9).

Cell uptake of carotenoids from micelles generated during digestion of oil enriched with individual carotenoids or mixtures of carotenoids: Caco-2 cells (HTB37; passages 25-28) obtained from ATCC (American Tissue Cell Culture) at passage 19 were maintained in 6-well plastic dishes. The cells were cultured in complete DMEM plus 15% heat inactivated FBS during replication phase. After confluency, FBS was decreased to 7.5% and media changed media every second day and the day before experimentation. The cultures were used for experiments at 11-14 dpc. Aqueous fraction from simulated digestion of test samples was diluted 1:4 with basal DMEM for making test media to treat cells. Each well of 6-well plastic dish was added 2 mL of test media and dishes were returned to cell culture incubator (5% CO2, 37° C.) for four hours. After exposure to test media for four hours, cells were harvested by washing 1× with cold PBS plus 2 g/L albumin and 2× with cold PBS. Cells were scrapped in 1.5 mL cold PBS and transferred into 15 mL polypropylene test tube. Cells pellet was collected by centrifugation at 800×g, 4° C. for 10 min. PBS was discarded then cell pellet was blank with nitrogen and stored at −20° C. for carotenoid analysis by HPLC within one week.

Example 3

Carotenoids—In Vitro Absorption

The interactions among beta-carotene (B), lutein (L), and astaxanthin (A) were examined using a Caco-2 cell model. The results are presented in Table 3.

In $BLA_{high}$ (A is 25% of total carotenoids), B absorption is 18.5% and increased by 20.92% compared to B absorption in B alone; L absorption is 34.1% and increased 5.88% compared L absorption in L alone. In $BLA_{low}$ (A is 12.5% of total carotenoids), B and L absorption show similar degree of increases compared to $BLA_{high}$.

% Carotenoid uptake=(carotenoid in the cell+carotenoid in Basal Lateral Compartment)*100%/carotenoid in test medium

TABLE 3

In-Vitro Carotenoid Cellular Uptake

| Treatment | Carotenoids in Sythetic Micelles nmol/50 ml | Carotenoid Ratio | % Carotenoid Cellular Uptake | | % Increase in Carotenoid Cellular Uptake Compared to Single Carotenoid | |
|---|---|---|---|---|---|---|
| | | | B | L | B | L |
| B | 50 | 100 | 15.30 | NA | 0.00 | NA |
| L | 25 | 100 | NA | 31.8 | NA | 0.00 |
| $B:L:A_{high}$ | 100 | 50:25:25 | 18.50 | 34.10 | 20.92 | 7.23 |
| $B:L:A_{low}$ | 87.5 | 57:29:14 | 18.50 | 34.10 | 20.92 | 7.23 |

Caco-2 human intestinal cells were grown and maintained on transwell inserts (3.0 μm pores) according to protocol in Failla M L., Chitchumroonchokchai C. (2005) In vitro models as tools for screening the relative bioavailabilities of provitamin A carotenoids in foods. HarvestPlus Technical Monograph Series 3. 32 p. www.harvestplus.org/pdfs/tech03.pdf. Cultures were used at 21 days post-confluency (dpc).

The stock synthetic micelles (SM) containing either β-carotene (B), lutein (L), or astaxanthin (A) was prepared as described by Chitchumroonchokchai et al. (2004).

Treated cells were incubated in humidified environment of 95% air, 5% $CO_2$ at 37° C. for 18 hours before spent medium in apical chamber (AP) and basolateral medium (BL) were collected. All samples were frozen at −80° C. under nitrogen until analysis. Carotenoid analysis in media and cells were quantified as described by Chitchumroonchokchai (See Chitchumroonchokchai C., Schwartz S J., Failla M L. Assessment of lutein bioavailability from meals and supplement using simulated digestion and Caco-2 human intestinal cells. J Nutr. 2004; 134:2280-2286). Protein content of cells was determined by the bicinchoninic acid assay (Pierce—www-.piercenet.com/files/1296 as8.pdf). Integrity of monolayers was determined by monitoring the rate of paracellular transport of phenol red (See Chitchumroonchokchai C., Schwartz S J., Failla M L. Assessment of lutein bioavailability from meals and supplement using simulated digestion and Caco-2 human intestinal cells. J Nutr. 2004; 134:2280-2286).

Example 4

Carotenoids—In Vitro Absorption

The interactions among beta-caroten (B), lutein (L) and astaxanthin (A) were examined using simulated digestion and Caco-2 cell model as described in Example 2. The final concentration of carotenoids in test medium were either 200 nmoL β-carotene or 200 nmoL lutein, as well as mixtures containing 100 nmoL β-carotene, 50 nmoL lutein and either 50 or 8 nmoL free (unesterified) astaxanthin. Monolayers of Caco-2 cells (12 dpc) were exposed to test compounds and incubated for 4 hours. Cells were harvested and extracted for analysis of cellular uptake by HPLC. Percent cellular uptake was calculated as pmol carotenoids in cells divided by the pmol carotenoid in 2 ml test medium.

The results are presented in Table 4. In BLAhigh (A is 25% of total carotenoids), B absorption is 20.9%. L absorption is 41.2%. In BLAlow (A is 5% of the total carotenoids), B absorption is 25.4%, L absorption is 46.9%.

TABLE 4

In Vitro Carotenoid Absorption

| Treatment | Added Amt nmol/50 ml | Carotenoid Ratio | % Carotenoid Cellular uptake | |
|---|---|---|---|---|
| | | | B | L |
| B:L:Ahigh | 200 | 100:50:50 | 20.90 | 41.20 |
| B:L:Alow | 158 | 100:50:08 | 25.40 | 46.90 |

Thus, as shown in Tables 1-4, an increase in absorption of the carotenoids occurs when astaxanthin (or astaxanthin ester) is combined with beta-carotene and/or lutein, even at relatively low amounts of the keto-carotenoid. This increase in absorption is shown both in vitro and in vivo.

Benefits

The carotenoid-containing compositions as disclosed herein may provide health benefits to companion animals. Benefits may include learning ability, optimal brain function, brain development, memory, neurological development, agility, alertness, cognitive ability, cognitive dysfunction, neurodegenerating disease, impaired neurotransmission, reduce ischemia-induced brain injury, preventing or decreasing age-related deterioration of mental/cognitive/memory decline, physical endurance and muscle recovery, endurance and reduce recovery time, running/walking/hunting time, number of stairs climbed, fat burning to provide muscle cells with energy, sensory benefit of clear vision, less cloudy eyes, less age-related retinal degeneration, reduce eye fatigue, hearing and smelling improvement skin improvement in UV protection, protect skin's natural antioxidant network and DNA, anti-inflammation of skin, skin and coat (reduce itchy skin and ear infection), oxidative stress (including reduced nucleic acid damage), immune response/body defense/disease resistance, vaccine response, mobility, joint/bone health, performance activity level, quality of life, frailty index, reduced inflammation, gastrointestinal (GI) benefits, modification of gut flora, reduced upset of GI, diarrhea, improved oxidative stress (as disclosed herein in Example 1), AOX status by AOX combinations, sustain AOX status in elderly pet or diarrhea conditions, renal health, kidney disease, maintain healthy weight, dental and gum health, prevention of cancer, cardioprotective and heart health, and prevention cardiovascular disease.

Additionally, embodiments of the invention also relate to a method of improving the health of a companion animal by administering the compositions disclosed herein. As is known, these carotenoids have health benefits to companion animals, and increasing the bioavailability of those carotenoids will thus in turn lead to increased health benefits.

Thus, as shown herein and demonstrated herein, the combinations of carotenoids disclosed herein can increase the bioavailability of the carotenoids, which can increase the health of the companion animal. In one specific embodiment, an improved protection against oxidative stress to dog peripheral blood lymphycytes occurs.

Methods

HPLC Analysis

HPLC analysis was performed as described in Lin W C, Chien J T, Chen B H. Determination of carotenoids in spear shrimp shells (*Parapenaeopsis hardwickii*) by liquid chromatography. J Agric Food Chem. 2005 Jun. 29; 53(13):5144-9. Fifty-microliter samples were injected onto the HPLC system. All procedures were performed under dim light and on ice.

Serum Carotenoids

The serum carotenoids level was measured as follows. Approximately 5 ml of non-fasting venous blood was drawn from each subject into serum separating tubes (BD, San Jose, Calif.). Blood samples were centrifuged at 5,000 rpm for 5 min at 4° C., and then the serum was removed and immediately stored at −70° C. until analysis. Carotenoids (lipid soluble) were extracted from 100 µl of serum based on previously reported methods by Khachik F et al (Khachik F, Spangler C J, Smith J C Jr, Canfield L M, Steck A, Pfander H. Identification, quantification, and relative concentrations of carotenoids and their metabolites in human milk and serum. Anal Chem. 1997 May 15; 69(10):1873-81). Briefly, 100 µl of serum was added to 200 µl 0.1% butylated hydroxytoluene (BHT) in ethanol to precipitate the proteins, and then 500 µl ethyl acetate was added to extract the carotenoids. The sample was centrifuged at 2,000×g for 5 min at 4° C., and the supernatant phase was collected. Then the sample was extracted with 500 µl ethyl acetate two more times and extracted with 500 µl hexane once. The collected supernatants were combined and dried down under vacuum. The dried sample was dissolved in 1 ml of 50% methanol and then extracted with 500 µl of hexane three times. The collected supernatants were then dried down and re-dissolved in 100 µl of running solvent prior to HPLC analysis.

Quantification of Carotene in a Food Composition

Carotene: The determination of carotene in a food composition by HPLC.

Equipment:
  HPLC with UV detection . . . Agilent 1100 series with PDA detector or equivalent
  Data System . . . Dionex Chromeleon Chromatography Data System or equivalent
  HPLC Column . . . ProntoSil C30; 3 m particle; 150 mm×4.6 mm; MacMod Scientific (Chads Ford, Pa.) #2546H300PS030
  Analytical Balance . . . Accurate to 0.0001 g
  Sample mill . . . Straub Model 4E electric powered Grinding Mill, 4B plates, worm drive
  Shaking Water Bath . . . Capable of maintaining a temperature of 70° C.±0.1 C.°; 50 strokes/min
  Centrifuge . . . With basket suitable for 50 mL centrifuge tubes; capable of 1750 rpm Consumables:
  Centrifuge Tubes . . . 50 mL capacity with caps; VWR #21020-695 or equivalent
  Sample Filter . . . Corning 0.45 µm Spin-X centrifuge filter; VWR #29442-762 or equivalent
  Autosampler vial . . . 2 mL; Amber vials with septum caps suitable for use with autosampler Reagents:
  Hexane . . . HPLC grade; J. T Baker #9304 or equivalent
  Ethyl Acetate . . . HPLC Grade; J. T. Baker #9282 or equivalent
  Acetone . . . HPLC Grade; J. T. Baker #9002 or equivalent
  Toluene . . . HPLC Grade; J. T. Baker #9351 or equivalent
  Ethanol . . . Apper Chemical, non-denatured
  Methanol . . . HPLC Grade; J. T. Baker #9093 or equivalent
  Methyl-t-butyl ether . . . HPLC Grade; J. T. Baker #9042 or equivalent
  Potassium Hydroxide . . . Reagent Grade; J. T. Baker #3140-01
  t-Butylhydroxytoluene . . . >99.0%; Sigma #C-4582
  Ethoxyquin . . . 90%, VWR #IC15796380
  trans-beta-carotene . . . Chromadex #CDXA-10-0385 (Irvine, Calif.) no substitute
  Purified water . . . Milli-Q purified water or equivalent Solutions:
    Extraction Solvent 1 . . . hexane (300 mL)+acetone (210 mL)+toluene (210 mL)+ethyl acetate (180 mL)+BHT (10 g)
    Extraction Solvent 2 . . . 75% hexane/25% ethyl acetate (v/v)
    Methanolic KOH . . . 40% KOH in methanol (w/v)
    10% Sodium Sulfate . . . 10% sodium sulfate in purified water (w/v)
    Mobile Phase . . . 75% methanol/25% methyl-t-butyl ether (v/v)

Procedure:
 1. Grind approximately 250 g to 300 g of sample using a Straub Grinding Mill.
 2. Accurately weigh 1.0 g of sample powder into a 50 mL glass centrifuge tube. Record mass to ±0.0001 g.
 3. Add 7.5 mL of the Extraction Solvent 1 to the sample and vortex for 1 min.
 4. Add 4 mL of 40% methanolic KOH solution sample and vortex for 1 min.
 5. Cap and place sample into shaking water bath for 60 min.
 6. Remove sample and allow to cool to room temperature.
 7. Add 7.5 mL of Extraction Solvent 2 and vortex for 1 min.
 8. Add 10 mL of 10% sodium sulfate solution and vortex for 1 min.
 9. Centrifuge for 8 min at 1750 rpm.
 10. Remove approximately 2 mL of organic layer and filter through a 0.45 μm Nylon filter.
 11. Accurately pipette 1.00 mL of filtrate into amber autosampler vial and dry under nitrogen.
 12. Accurately pipette 1.00 mL of mobile phase into amber autosampler vial and vortex for 1 min.

HPLC Conditions:
    Flow rate . . . 1.7 mL/min. isocratic
    Run Time . . . 20 min
    Injection volume . . . 100 μL
    Column temperature . . . 25° C.
    Detection . . . 452 nm
    Approximate retention times:

| | |
|---|---|
| 4.3 min | 15-cis-beta-carotene |
| 4.7 min | 13-cis-beta-carotene |
| 5.3 min | trans-α-carotene |
| 6.25 min | trans-beta-carotene |
| 7.20 min | 9-cis-beta-carotene |

Calibration:
 1. Calibration with a trans-beta-carotene standard are performed a minimum of once per year or whenever the system is changed.
    a. All standards are prepared in the mobile phase.
    b. Measured masses are corrected for Adjusted Purity from the Certificate of Analysis.
    c. Calibration is based on a three point standard curve ranging from 0.1 to 1.0 μg/mL using least squares, linear regression fit forced through zero.
    d. The same response curve is applied to all carotene isomers.
 2. During calibration, a 1 μg/mL trans-beta-carotene quality control standard containing 100 ppm ethoxyquin, is prepared and stored at −20° C. The QC standard is injected with each sample set to verify system suitability.

Lutein: The determination of lutein in a food composition by HPLC.

Equipment:
    HPLC with UV detection . . . Agilent 1100 series with PDA detector or equivalent
    Data System . . . Dionex Chromeleon Chromatography Data System or equivalent
    HPLC Column . . . Phenomenex Luna Silica (2) column; 5 m particle; 150 mm×4.6 mm; Phenomenex (Torrance, Calif.) #00E-4043-E0
    Analytical Balance . . . Accurate to 0.0001 g
    Sample Mill . . . Straub Model 4E electric powered Grinding Mill, 4B plates, worm drive
    Shaking Water Bath . . . Capable of maintaining a temperature of 70° C.±0.1 C.°; 50 strokes/min
    Centrifuge . . . With basket suitable for 50 mL centrifuge tubes; capable of 1750 rpm Consumables:
    Centrifuge Tubes . . . 50 mL capacity with caps; VWR 21020-695 or equivalent
    Sample Filter . . . Corning 0.45 μm Spin-X centrifuge filter; VWR 29442-762 or equivalent
    Autosampler vial . . . 2 mL; amber vials with septum caps suitable for use with autosampler Reagents:
    Hexane . . . HPLC grade; J. T Baker #9304 or equivalent
    Ethyl Acetate . . . HPLC Grade; J. T. Baker #9282 or equivalent
    Acetone . . . HPLC Grade; J. T. Baker #9002 or equivalent
    Toluene . . . HPLC Grade; J. T. Baker #9351 or equivalent
    Ethanol . . . Apper Chemical, non-denatured
    Methanol . . . HPLC Grade; J. T. Baker #9093 or equivalent
    Potassium Hydroxide . . . Reagent Grade; J. T. Baker #3140-01
    Butylhydroxytoluene . . . >99.0%; Sigma #C-4582
    Ethoxyquin . . . 90%, VWR #IC15796380
    Lutein . . . Chromadex #CDXA-08-0549 (Irvine, Calif.) no substitute
    Purified water . . . Milli-Q purified water or equivalent Solutions:
    Extraction Solvent 1 . . . hexane (300 mL), acetone (210 mL), toluene (210 mL), ethyl acetate (180 mL), BHT (10 g)
    Extraction Solvent 2 . . . 75% hexane/25% ethyl acetate (v/v)
    Methanolic KOH . . . 40% KOH in methanol (w/v)
    10% Sodium Sulfate . . . 10% sodium sulfate in purified water (w/v)
    Mobile Phase . . . 65% hexane/30% ethylacetate, 5% acetone (v/v/v)

Procedure:
 1. Grind approximately 250 g to 300 g of sample using a Straub Model 4E Grinding Mill.
 2. Accurately weigh 1.0 g of sample powder into a 50 mL glass centrifuge tube. Record mass to ±0.0001 g.
 3. Add 7.5 mL of the Extraction Solvent 1 to the sample and vortex for 1 min.
 4. Add 4 mL of 40% methanolic KOH solution sample and vortex for 1 min.
 5. Cap and place sample into shaking water bath for 60 min.
 6. Remove sample and allow to cool to room temperature
 7. Add 7.5 mL of Extraction Solvent 2 and vortex for 1 min.
 8. Add 10 mL of 10% sodium sulfate solution and vortex for 1 min.
 9. Centrifuge for 8 min at 1750 rpm.
 10. Remove approximately 2 mL of organic layer and filter through a 0.45 m Nylon filter.

HPLC Conditions:
  Flow rate . . . 1.5 mL/min isocratic
  Run Time . . . 15 min
  Injection volume . . . 100 μL
  Column temperature . . . 25° C.
  Detection . . . 452 nm
  Approximate retention times:

| | |
|---|---|
| 5.5 min. | trans lutein |
| 7.0 min | 9-cis lutein |
| 7.3 min. | 13-cis lutein |
| 8.0 min. | 15-cis lutein |

Calibration:
  1. Calibrations with the trans lutein standard are performed a minimum of once per year or whenever the system is changed.
    a. All standards are prepared in the mobile phase.
    b. Measured masses are corrected for Adjusted Purity from the Certificate of Analysis.
    c. Calibration is based on a three point standard curve ranging from 0.1 to 1.0 μg/mL using least squares, linear regression fit forced through zero.
    d. The same response curve is applied to all lutein isomers.
  2. During calibration, a 1 μg/mL trans lutein quality control standard containing 100 ppm ethoxyquin, is prepared and stored at −20° C. The QC standard is injected with each sample set to verify system suitability.

Astaxanthin: The determination of astaxanthin in a food composition by HPLC.

This method is based on the method titled "Spectrophotometric and HPLC Analysis Method for Determining astaxanthin Content in AstaREAL® L10" as published at www.astareal.com by Fuji Chemical Industry Co., Ltd. Esterified astaxanthin must first be hydrolyzed (deesterified) completely by enzymatic procedure to yield all free astaxanthin.

Reagents and Equipment:
  0.05M Tris-HCl buffer (pH7.0)
  Cholesterol esterase: Wako Pure Chem., cat#037-11221 or Sigma, cat#: C9281
  Trans-beta-apo-8'-carotenal, Fluka cat#: 10829 [internal standard for HPLC analysis]
  Astaxanthin: Wako Pure Chem., cat#019-18663 or Sigma, cat# A9335 [analytical standard]
  1% (v/v) phosphoric acid solution
  Acetone, Spectrophotometric grade
  Hexane, HPLC grade
  Petroleum ether
  Methanol, analytical grade
  MTBE: t-butyl-methyl-ether, spectrophotometric grade
  Sodium sulfate decahydrate
  Sodium sulfate anhydrous
  10 mL centrifuge tubes
  20 mL volumetric flasks
  50 mL volumetric flasks
  100 mL volumetric flasks
  200 mL volumetric flasks
  1.0 mL volumetric pipettes
  2.0 mL volumetric pipettes
  5.0 mL volumetric pipettes
  10.0 mL volumetric pipettes
  0.45 um syringe filter
  Water bath
  Analytical balance
  Centrifuge
  Sonicator
  Spectrophotometer
  HPLC equipped with a UV/VIS detector
  HPLC column: YMC-Carotenoid™ S5 micron, 250 mm length×4.6 mm dia.

Procedure:
Cholesterol Esterase Solution for hydrolysis of Astaxanthin Esters:
  Dissolve an accurately weighed quantity of cholesterol esterase (Wako Pure Chem., Cat #: 037-11221 or Sigma, cat#: C9281) in 50 mM Tris-HCl (ph 7.0) having a known concentration of 4 units per mL.

Internal Standard Preparation:
  Accurately weigh about 7.5 mg of trans-beta-apo-8'-Carotenal (Fluka, Cat #: 10829, >20% (UV-VIS) Apocarotenal) and transfer into a 200 mL-volumetric flask.
  Dissolve in aceton, dilute with acetone to volume, and mix.

Standard Preparation:
  Transfer about 5 mg of Astaxanthin reagents (Wako Pure Chem., cat#019-18663 or Sigma, Cat #: A9335) to a 200 mL-volumetric flask, dissolve in about 100 mL of acetone, sonicate for a minute in warm water, and allow to equilibrate to ambient temperature for 15 minutes.
  Dilute with acetone to volume and mix (Standard stock solution).
  Pipette 2.0 mL of Standard stock solution to a 20-mL volumetric flask, dilute with acetone to volume, and mix (Standard solution A).
  Pipette 2.0 mL of Standard stock solution and 10.0 mL of Internal standard solution to a 20 mL-volumetric flask, dilute with acetone to volume, and mix (Standard solution B).

Assay Preparation:
  Warm AstaREAL® L10 in a pre-heated water bath at 50-60° C. for 30 minutes. Shake very well at 10 minute intervals.
  Transfer approximately 30 mg of AstaREAL® L10 to a 10-mL glass tube, add approximately* 5 mL of acetone to dissolve AstaREAL® L10. *Note the exact weight.
  Pipette the AstaREAL® L10 solution from the glass tube into a 100-mL volumetric flask. Rinse the tube with more acetone to recover all remaining orange color. For each additional rinse, add 5 mL of acetone into the tube, gently swirl, and pipette contents into the flask. Make-up the final volume to 100 mL with acetone, this stock is the sample stock.
  Pipette 2.0 mL of the sample stock into a 20-mL volumetric flask, dilute with acetone to volume, and mix (Assay solution A).
  Transfer 2.0 mL Assay solution A to a 10-mL glass centrifuge tube, add 1.0 mL of I.S. solution, and mix.
  Set block heater at 37° C., add 3.0 mL of Cholesterol esterase solution to the test tube, and mix by gentle inversion.
  Allow to react at 37° C. for 45 minutes. Gently/slowly invert every 10 minutes, at least twice, during the reaction.
  Add 1 g of sodium sulfate decahydrate and 2 mL of petroleum ether, vortex for 30 seconds, and centrifuge at 3,000 rpm for 3 minutes.
  Transfer the petroleum ether layer to a 10-mL glass centrifuge tube containing 1 g of sodium sulfate anhydrate.
  Evaporate the petroleum ether layer in vacuo or in the stream of inert gas at room temperature, add 3 mL of acetone, sonicate, and filter (Assay solution B).

Reversed-phase HPLC Analysis Method for Astaxanthin Content:
  Determine the absorbance of Standard solution A at 474 nm, using acetone as the blank.
  Run the mobile-phase through the HPLC conditions as specified in HPLC Table 1 before sample analysis.

Analyze an aliquot of Standard solution B and Assay solution B by HPLC under the following conditions:
HPLC Table:
Detector: UV/VIS detector, at 474 nm
Column: YMC-Carotenoid™ S5μ, 4.6×250 mm
Column temp: 25° C.
Flow rate: 1.0 mL/minute
Injection vol.: 20 μL
Mobile phase: Methanol, t-Butylmethylether, 1% Phosphoric acid aqueous
Mobile phase formula (%) is as follows:

| Time (min.) | Methanol | t-Butylmethylether | 1% Phosphoric acid aqueous |
|---|---|---|---|
| 0 | 81 | 15 | 4 |
| 15 | 66 | 30 | 4 |
| 23 | 16 | 80 | 4 |
| 27 | 16 | 80 | 4 |
| 27.1 | 81 | 15 | 4 |
| 35 | 81 | 15 | 4 |

Retention time for Identification:

| Components | Retention time (min.) |
|---|---|
| 13-cis-astaxanthin | 9 |
| trans-astaxanthin | 10 |
| 9-cis-astaxanthin | 14 |
| trans-beta-apo-8'-carotenal | 17 |

(Internal Standard)
Calculate the concentration, in mg per mL, of astaxanthin in the Standard solution A taken by the formula: ASa/210
in which ASa is the absorbance of Standard solution A, and 210 is absorbance of a 1 (mg/mL) astaxanthin solution in acetone, in a 1 cm cuvette at 474 nm. The expected absorbance of Standard solution A is 0.525, which is equivalent to 5 mg of astaxanthin standard reagent in 2000 mL-dilution volume.
Calculate the ratios of peak responses of total astaxanthin to I.S. obtained from the Assay solution B and Standard solution B taken by the formula: $(1.3P_{13\text{-}cis}+P_{trans}+1.1P_{9\text{-}cis})/P_{IS}$
in which $P_{13\text{-}cis}$, $P_{trans}$, $P_{9\text{-}cis}$, and $P_{IS}$ are the peak responses of 13-cis-, trans-, 9-cis-astaxanthin isomers and IS, respectively, and 1.3 and 1.1 are the relative response coefficients of 13-cis-, and 9-cis-astaxanthin to transastaxanthin, respectively.
Calculate the Astaxanthin Content (% w/w) in AstaREAL® L10 taken by the formula: $C_{SA}(R_{AB}/R_{SB})*1000/W*100$
in which $C_{SA}$ is the concentration, in mg per mL, of astaxanthin in the Standard solution A, 1000 is dilution volume for Assay preparation, W is the weight, in mg, of the AstaREAL® L10 specimen taken for the Assay solution preparation, and $R_{AB}$ and $R_{SB}$ are the ratios of the peak responses of total astaxanthin to IS obtained from the Assay solution B and the Standard solution B, respectively.
DNA Damage
DNA damage was detected by single cell gel electrophoresis (comet assay) based on the method of Shen S et al (Shen S, Cooley D M, Glickman L T, Glickman N, Waters D J. Reduction in DNA damage in brain and peripheral blood lymphocytes of elderly dogs after treatment with dehydroepiandrosterone (DHEA). Mutat Res. 2001 Sep. 1; 480-481:153-62).

To determine the extent of basal DNA damage, PBLs were suspended in low melting point agarose in PBS at 37° C. and pipetted onto a glass microscope slide pre-coated with a layer of normal melting point agarose. The final layer was comprised of 80 μl of low melting agarose alone. After solidification of the agarose, slides were immersed in cold lysing solution (2.5 M NaCl, 100 mM Na$_2$-EDTA, 10 mM Tris and 300 mM NaOH to adjust the pH to 10.0, 10% DMSO and 1% Triton X-100 added fresh) and stored in the dark overnight at 4° C. Slides were then removed from the lysing solution and placed on a horizontal gel electrophoresis tank (Fisher, Fair Lawn, N.J.) containing freshly prepared alkaline buffer (300 mM NaOH and 1 mM Na$_2$-EDTA, pH>13). Slides remained submerged in buffer for 20 min before electrophoresis at 25 V and 300 mA for 30 min. Slides were then washed three times (5 min each) with 0.4 M Tris at pH 7.5. After the final wash, slides were drained and exposed to cold 100% ethanol to dry. All steps from cell lysis until the end of neutralization were performed in the dark or under yellow light. Each slide was stained with 150 μl of SYBR Green 1 (1:10,000 dilution in TE buffer at pH 7.5) prior to analysis. To determine if treatment of dogs with antioxidants affected the sensitivity of their PBLs to oxidant stress, freshly isolated PBLs from each dog were exposed to 25 μM H$_2$O$_2$ for 5 min at 4° C. prior to suspension in agarose and electrophoresis. Each cell was visually scored on a 0-4 scale as follows:
no damage (type 0);
mild to moderate damage (type 1 & 2),
extensive DNA damage (type 3 & 4).
Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.
While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A pet food composition comprising at least three carotenoids, the at least three carotenoids consisting essentially of an astaxanthin ester, a beta-carotene, a lutein, and a pet food composition, wherein the pet food composition is selected from the group consisting of daily feed, wet food, supplements, treats, and combinations thereof, and wherein said pet food composition comprises a meat protein source selected from the group consisting of casein, albumin, beef, pork, lamb, poultry, fish, and mixtures thereof; said composition being further characterized in that:
   i) the ratio of the beta-carotene to the lutein to the to the astaxanthin ester is from about 1:1:0.6 to about 10:1:3.5; or
   ii) the ratio of the beta-carotene to the lutein to the to the astaxanthin ester is from about 1:1:0.6 to about 1:10:3.5 ii) the ratio of the beta-carotene to the lutein to the to the astaxanthin ester is from about 1:1:0.002 to about 10:1:0.1; or iii) the ratio of the beta-carotene to the lutein to the to the astaxanthin ester is from about 1:1:0.002 to about 1:10:0.1.

* * * * *